DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED AUGUST 31, 1971

889 O.G. 1363

T889,009

N - ISOPROPYL-N-CYCLOHEXYLTHIOCARBAMYL-N,N'-DIMETHYLSULFENAMIDE AS A VULCANIZATION ACCELERATOR

Adel F. Halasa, 1568 Larch St., Akron, Ohio 44301

Continuation of abandoned application Ser. No. 868,648, Sept. 22, 1969, which is a continuation of abandoned application Ser. No. 733,776, June 3, 1968, which in turn is a continuation of application Ser. No. 528,783, Feb. 21, 1966. This application July 13, 1970, Ser. No. 56,211

Int. Cl. C07c *155/04;* C08f *27/06*

U.S. Cl. 260—79.5B

No Drawing. 11 Pages Specification

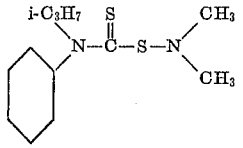

N - isopropyl-N-cyclohexylthiocarbamyl-N,N'-dimethylsulfenamide is an accelerator of the vulcanization of diolefin rubbers, including butadiene-styrene, polybutadiene and polyisoprene rubbers, said accelerator has the following structure: